US007622454B2

(12) United States Patent
Shepard et al.

(10) Patent No.: US 7,622,454 B2
(45) Date of Patent: Nov. 24, 2009

(54) RNAI INHIBITION OF CTGF FOR TREATMENT OF OCULAR DISORDERS

(75) Inventors: Allan R. Shepard, Fort Worth, TX (US); Iok-Hou Pang, Grand Prairie, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 11/313,200

(22) Filed: Dec. 19, 2005

(65) Prior Publication Data

US 2006/0166919 A1 Jul. 27, 2006

Related U.S. Application Data

(60) Provisional application No. 60/638,705, filed on Dec. 23, 2004.

(51) Int. Cl.
*A61K 48/00* (2006.01)
*C07H 21/02* (2006.01)
*C07H 21/04* (2006.01)
(52) U.S. Cl. .................. 514/44; 536/23.1; 536/24.5
(58) Field of Classification Search ............ None
See application file for complete search history.

(56) References Cited

U.S. PATENT DOCUMENTS

| | | | |
|---|---|---|---|
| 5,585,270 A | 12/1996 | Grotendorst et al. | |
| 5,734,039 A * | 3/1998 | Calabretta et al. | 536/24.5 |
| 6,069,006 A | 5/2000 | Grotendorst et al. | |
| 6,326,193 B1 | 12/2001 | Liu et al. | |
| 6,348,329 B1 | 2/2002 | Schmidt et al. | |
| 6,358,741 B1 | 3/2002 | Schmidt et al. | |
| 6,506,559 B1 * | 1/2003 | Fine et al. | 435/6 |
| 2002/0086356 A1 | 7/2002 | Tuschl et al. | |
| 2002/0114784 A1 | 8/2002 | Li et al. | |
| 2002/0162126 A1 | 10/2002 | Beach et al. | |
| 2003/0027783 A1 | 2/2003 | Zernicka-Goetz et al. | |
| 2003/0153524 A1 * | 8/2003 | Hinton et al. | 514/44 |
| 2004/0005319 A1 | 1/2004 | Grotendorst et al. | |
| 2004/0053411 A1 | 3/2004 | Cullen et al. | |
| 2004/0092450 A1 | 5/2004 | Grotendorst et al. | |
| 2004/0147475 A1 | 7/2004 | Li et al. | |
| 2004/0175732 A1 | 9/2004 | Rana | |
| 2004/0203145 A1 | 10/2004 | Zamore et al. | |
| 2004/0235031 A1 * | 11/2004 | Schultz et al. | 435/6 |

FOREIGN PATENT DOCUMENTS

| | | | | |
|---|---|---|---|---|
| CA | 2359180 | | 7/2001 | |
| WO | WO 94/01550 | * | 1/1994 | 514/44 |
| WO | WO 00/44895 | | 8/2000 | |
| WO | WO 01/36646 A1 | | 5/2001 | |
| WO | WO 01/68836 A3 | | 9/2001 | |
| WO | WO 02/44321 A3 | | 6/2002 | |
| WO | WO 03/049773 A1 | | 6/2003 | |
| WO | WO 03/092584 A2 | | 11/2003 | |
| WO | WO 2004/022782 A2 | | 3/2004 | |
| WO | WO 2004/031237 A1 | * | 4/2004 | 514/44 |
| WO | WO 2004/065546 A2 | | 8/2004 | |
| WO | WO 2005/079815 A2 | | 9/2005 | |
| WO | WO 2005/083083 A3 | | 9/2005 | |

OTHER PUBLICATIONS

Elbashir et al., Functional anatomy of siRNAs for mediating efficienct RNAi in *Drosophila melanogaster* embryo lysate, 2001, The EMBO Journal, vol. 20, No. 23, pp. 6877-6888.*
Hammond et al., Post-Transcriptional Gene Silencing by Double-Stranded RNA, 2001, Nature Reviews, Genetics, vol. 2, pp. 110-119.*
Zhang et al., Targeted Gene Silencing by Small Interfering RNA-Based Knock-Down Technology, 2004, Current Pharmaceutical Biotechnology, vol. 5, p. 1-7.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Scherer et al., Approaches for the sequence-specific knockdown of mRNA, 2003, Nat. Biotechnol., 21(12), pp. 1457-1465.*
Tuschl et al., The siRNA user guide, Aug. 26, 2001 (on-line), retrieved Jan. 31, 2002, Max Planck Institute for Biophysical Chemistry, pp. 1, 3 and 5, http://www.mpibpc.gwdg.de/abteilungen/100/105/siRNAuserguide.pdf.*
Holen et al., Positional effects of short interfering RNAs targeting the human coagulation trigger Tissue Factor, 2002, Nucleic Acids Research, vol. 30, No. 8, pp. 1757-1766.*
Luo et al., The gene-silencing efficiency of siRNA is strongly dependent on the local structure of mRNA at the targeted region, 2004, Biochemical and Biophysical Research Communications, 318, pp. 303-310.*
Ambros, "The functions of animal microRNAs", *Nature*, pp. 350-355, vol. 431, Sep. 16, 2004, © 2004, Nature Publishing Group.
Bartel, "MicroRNAs: Genomics, Biogenesis, Mechanism, and Function", *Cell*, pp. 281-297, vol. 116, Jan. 23, 2004, © 2004, Cell Press.
Croci, et al., "Inhibition of Connective Tissue Growth Factor (CTGF/CCN2) Expression Decreases the Survival and Myogenic Differentiation of Human Rhabdomyosarcoma Cells", pp. 1730-1736, vol. 64, Cancer Research, Mar. 1, 2004.
Dorsett, et al., "SiRNAs: Applications in Functional Genomics and Potential as Therapeutics", *Nature*, pp. 318-329, vol. 3, Apr. 2004, © 2004, Nature Publishing Group.
Echeverri, et al., "siRNA Design: It's All in the Algorithm", *AmbIon TechNotes*, pp. 1-6, vol. 11:3, http://www.ambion.com/techlib/tn/113/14.html.
Elbashir, et al., "Duplexes of 21—nucleotide RNAs Mediate RNA Interference in Cultured Mammalian Cells", *Letters to Nature*, pp. 494-498, vol. 411, May 24, 2001, © 2001, McMillan Magazines Ltd.

(Continued)

*Primary Examiner*—Amy Bowman
(74) *Attorney, Agent, or Firm*—Jason J. Derry

(57) ABSTRACT

RNA interference is provided for inhibition of connective tissue growth factor mRNA expression in ocular disorders involving CTGF expression. Ocular disorders involving aberrant CTGF expression include glaucoma, macular degeneration, diabetic retinopathy, choroidal neovascularization, proliferative vitreoretinopathy and wound healing. Such disorders are treated by administering interfering RNAs of the present invention.

10 Claims, 3 Drawing Sheets

OTHER PUBLICATIONS

Elbashir, et al., "Functional Anatomy of siRNAs for Mediating Efficient RNAi in *Drosophila melanogaster* embryo lysate", *The EMBO Journal*, pp. 6877-6888, vol. 20, No. 23, 2001, © European Molecular Biology Organization.

Elbashir, et al., "RNA interference is mediated by 21- and 22-nucleotide RNAs", *Genes & Development*, pp. 188-200, vol. 15, © 2001 Cold Spring Harbor Laboratory Press, ISSN 0890-9369/01.

Elbashir, et al., "Analysis of gene function in somatic mammalian cells using small interfering RNAs", *Methods*, pp. 199-213, vol. 26, © 2002 Elsevier Science (USA).

Hannon, et al, "Unlocking the potential of the human genome with RNA interference", *Nature*, pp. 371-378, vol. 431, Sep. 16, 2004, © 2004, Nature Publishing Group.

He, et al., "MicroRNAs: Small RNAs With A Big Role In Gene Regulation", *Reviews*, pp. 522-531, vol. 5, Jul. 2004, www.nature.com/reviews/genetics.

Kawasaki, et al., "Induction of DNA methylation and gene silencing by short interfering RNAs in human cells", *Nature*, pp. 211-217, vol. 431, Sep. 9, 2004, © 2004, Nature Publishing Group.

Lim, et al., "Vertebrate MicroRNA Genes", *Science*, pp. 1540, vol. 299, Mar. 7, 2003, www.sciencemag.org.

Liu, et al., "Argonaute2 is the Catalytic Engine of Mammalian RNAi", *Science*, pp. 1437-1441, vol. 305, Sep. 3, 2004, www.sciencemag.org.

Morris, et al., "Small Interfering RNA-Induced Transcriptional Gene Silencing in Human Cells", *Science*, pp. 1289-1292, vol. 305, Aug. 27, 2004, www.sciencemag.org.

NCBI Sequence NM_001901, "*Homo sapiens* connective tissue growth factor (CTGF), mRNA." pp. 1, 11, 12 & 13, http://www.ncbi.nlm.nih.gov, printed Nov. 11, 2005.

NCBI Sequence AK092280, "*Homo sapiens* cDNA FLJ34961 fis, clone NTONG2003839, highly similar to Connective Tissue Growth Factor Precursor." pp. 1-3, http://www.ncbi.nlm.nih.gov, printed Nov. 11, 2005.

NCBI Sequence AK125220, "*Homo sapiens* cDNA FLJ43230 fis, clone HCHON2001269, highly similar to Connective Tissue Growth Factor Precursor." pp. 1-3, http://www.ncbi.nlm.nih.gov, printed Nov. 11, 2005.

NCBI Sequence AY395801, "*Homo sapiens* connective tissue growth factor (CTGF) mRNA, complete cds." pp. 1-2, http://www.ncbi.nlm.nih.gov, printed Nov. 11, 2005.

NCBI Sequence AY550024, "*Homo sapiens* connective tissue growth factor mRNA, complete cds." pp. 1-2, http://www.ncbi.nlm.nih.gov, printed Nov. 11, 2005.

NCBI Sequence BT019794, "*Homo sapiens* connective tissue growth factor mRNA, complete cds." pp. 1-2, http://www.ncbi.nlm.nih.gov, printed Nov. 11, 2005.

NCBI Sequence BT019795, "*Homo sapiens* connective tissue growth factor mRNA, complete cds." pp. 1-2, http://www.ncbi.nlm.nih.gov, printed Nov. 11, 2005.

NCBI Sequence CR541759, "*Homo sapiens* full open reading frame cDNA clone RZPDo834G1037D for gene CTGF, connective tissue growth factor; complete cds, without stopcodon" pp. 1-2, http://www.ncbi.nlm.nih.gov, printed Nov. 11, 2005.

NCBI Sequence M92934, "*Homo sapiens* connective tissue growth factor mRNA, complete cds." pp. 1-2, http://www.ncbi.nlm.nih.gov, printed Nov. 11, 2005.

NCBI Sequence U14750, "Human connective tissue growth factor mRNA, partial cds." pp. 1-3, http://www.ncbi.nlm.nih.gov, printed Nov. 11, 2005.

NCBI Sequence X78947, "*H. sapiens* mRNA for connective tissue growth factor." pp. 1-2, http://www.ncbi.nlm.nih.gov, printed Nov. 11, 2005.

Novina, et al., "The RNAi revolution", *Nature*, pp. 161-164, vol. 430, Jul. 8, 2004, © 2004, Nature Publishing Group.

Paddison, et al., "Short hairpin RNAs (shRNAs) induce sequence-specific silencing in mammalian cells", *Genes & Development*, pp. 948-958, vol. 16, © 2002, Cold Spring Harbor Laboratory Press, ISSN 0890-9369/02.

Pang, et al, "Preliminary characterization of a transformed cell strain derived from human trabecular meshwork", *Current Eye Research*, pp. 51-63, vol. 13, No. 1, 1994, © Oxford University Press.

Poy, et al, "A pancreatic islet-specific microRNA regulates insulin secretion", *Letters to Nature*, pp. 226-230, vol. 432, Nov. 11, 2004, © 2004, Nature Publishing Group.

"psiRNA System A simple and innovative tool to create Short Hairpin SiRNAs" Small Interfering RNAs (siRNA) : psiRNA System, pp. 1-3, http://www.invivogen.com/siRNA/psiRNA_system.htm, printed Nov. 3, 2004.

"RNAi Shows Cracks in Its Armor", *Science*, pp. 1124-1125, vol. 306, Nov. 12, 2004, www.sciencemag.org.

"Selection of siRNA duplexes from the target mRNA sequence", *The siRNA user guide* (revised May 6, 2004), pp. 1-7, Tuschl Lab, http://www.rockerfeller.edu/labheads/tuschl/sima.html plus one page of supplementary information.

Shepard, at al., "Importance of quantitative PCR primer location for short interfering RNA efficacy determination", *Analytical Biochemistry*, pp. 287-288, vol. 344, © 2005, Elsevier Inc.

"siRNA Design Guidelines", Ambion Technical Bulletin #506, pp. 1-8, © 2004, Ambion, Inc. http://www.ambion.com/techlib/tb/tb_506.html.

"Small Interfering RNAs (siRNA) A revolution in functional genomics", Small Interfering RNAs (siRNA): Overview, pp. 1-3, http://www.invivogen.com/siRNA/siRNA_overview.htm, printed Nov. 3, 2004.

Soutschek, et al., "Therapeutic silencing of an endogenous gene by systemic administration of modified SiRNAs", *Nature*, pp. 173-178, vol. 432, Nov. 11, 2004, © 2004, Nature Publishing Group.

Wahab, et al., "Role of connective tissue growth factor in the pathogenesis of diabetic neuropathy", *Biochem. Journal*, pp. 77-87, vol. 359, © 2001, Biochemical Society.

Wang, et al., "Connective tissue growth factor SiRNA modulates mRNA levels for a subset of molecules in normal and TGF-$\beta_1$-stimulated porcine skin fibroblasts", *Wound Repair and Regeneration*, pp. 205-216, vol. 12, No. 2, Mar.-Apr. 2004, © 2004, the Wound Healing Society, ISSN: 1067-1927.

Ambion, Inc.; Sima Sequence NM_001901, "CTGF, Human," http://www.ambion.com/catalog/sima_search.php; date unknown.

Ambion, Inc.; "Matched SiRNAs and Assays," Technotes, vol. 11, No. 4, www.ambion.com/techlib/tn/14/4..html; date unknown, ISR states Jul. 2004.

Croci S. et al.; "Inhibition of Connective Tissue Growth Factor (CTGF/CCN2) Expression Decreases The Survival and Myogenic Differentiation of Human Rhabdomyosarcoma Cells," *Cancer Research*, pp. 1730-1736, vol. 64, No. 5, Mar. 2004.

Fuchshofer R. et al.; "Transforming Growth Factor-Beta2 Modulated Extracellular Matrix Component Expression in Cultured Human Optic Nerve Head Astrocytes," *Investigative Ophthalmology & Visual Science*, pp. 568-578, vol. 46, No. 2, Feb. 2005.

Shepard et al.; "Importance of Quantitative PCR Primer Location for Short Interfering RNA Efficacy Determination," *Analytical Biochemistry*, pp. 287-288, vol. 344, No. 2, Jun. 21, 2005 (online) and Sep. 15, 2005, Academic Press, New York NY.

Wang et al.; "Connective Tissue Growth Factor SiRNA Modulates mRNA Levels For a Subset of Molecules in Normal and TGF-Beta1-Stimulated Porcine Skin Fibroblasts," *Wound Repair and Regeneration*, pp. 205-216, vol. 12, No. 2, Mar. 2004.

Welge-Lussen et al.; "CTGF is the Fibrogenic Mediator of TGF-beta in PVR Disease," *102. Jahrestagung der Dog Duetsche Ophthalmologische Gesellschaft e.V.*, 23 bis, Sep. 26, 2004, Berlin, Germany, www.egms.de/en/meetings/dog2004/04dog159.html.

PCT International Search Report, PCT/US2005/046064, mailed May 26, 2006.

PCT Written Opinion of the International Searching Authority, PCT/US2005/046064, mailed May 26, 2006.

Jampel, Henry D., et al.; Transforming growth factor-beta in human aqueous humor; Current Eye Research, 1990, pp. 963-969; vol. 9, No. 10.

Tripathi, Junping Li, et al; Aqueous Humor in Glaucomatous Eyes Contains an Increased Level of TGF-beta2; Exp. Eye Res. (1994) 59.723-728.

Inatani, Masaru, et al., Transforming growth factor-beta2 levels in aqueous humor of glaucomatous eyes; Graefe's Arch Clin Exp. Ophthalmol; 2001; 239:109-113.

Koliakos, George G., et al.; Transforming and insulin-like growth factors in the aqueous humour of patients with exfoliation syndrome; Graefe's Arch Clin Exp Opththalmol; 2001; 239:482-487.

Ochiai, Yuko, et al.; Higher Concentration of Transforming Growth Factor-beta in Aqueous Humor of Glaucomatous Eyes and Diabetic Eyes; Jpn J Ophthalmol 46, 2002; 249-253.

Picht, G., et al.; Transforming growth factor beta-2 levels in the aqueous humor in different types of glaucoma and the relation to filtering bleb development; Graefe's Arch Clin Exp Ophthalmol; 2001; 239:199-207.

Schloetzer-Schrehardt, Ursula, et al; Role of Transforming Growth Factor-beta1 and its Latent Form Binding Protein in Pseudoexfoliation Syndrome; Exp. Eye Res; 2001; 73, 765-780.

Yamamoto, Naoki, et al.; Concentration of Transforming Growth Factor beta2 in Aqueous Humor; Ophthalmic Research; 2005; 37:29-33.

Fleenor, Debra L., et al.; TGF beta2-Induced Changes in Human Trabecular Meshwork: Implications for Intraocular Pressure; Investigative Ophthalmology & Visual Science; Jan. 2006; vol. 47, No. 1; pp. 226-234.

Schwarz, Dianne S., et al.; Asymmetry in the Assembly of the RNAi Enzyme Complex; Cell; vol. 115, 199-208, Oct. 17, 2003.

Smart, Nicola, et al.; A rapid and sensitive assay for quantification of siRNA efficiency and specificity; Biol. Proced. Online 2005; 7(1):1-7.

Ui-Tei, Kumiko, et al.; Guidelines for the selection of highly effective siRNA sequences for mammalian and chick RNA interference; Nucleic Acids Res. 32:936-948, 2004.

Vickers, Timothy A., et al.; Efficient Reduction of Target RNAs by Small Interfering RNA and RNase H-dependent Antisense Agents; Journal of Biological Chemistry; vol. 278, No. 9, pp. 7108-7118; 2003.

Warashina, Masaki, et al.; RNA-protein hybrid ribozymes that efficiently cleave any mRNA independently of the structure of the target RNA; pnas.org; May 8, 2001; vol. 98, No. 10; pp. 5572-5577.

Harborth, Jens, et al; Sequence, Chemical, and Structural Variation of Small Interfering RNAs and Short Hairpin RNAs and the Effect on Mammalian Gene Silencing; Antisense and Nucleic Acid Drug 13:83-105 (2003); USA.

Heale, Bret S. E., et al.; siRNA target site secondary structure predictions using local stable substructures; Nucleic Acids Research, 2005, vol. 33, No. 3; USA.

Kawasaki, Hiroaki, et al.; Identification of genes by hybrid ribozymes that couple cleavage activity with the unwinding activity of an endogenous RNA helicase; scientific report; 2002; Japan.

Khvorova, Anastasia, et al.; Functional siRNAs and miRNAs Exhibit Strand Bias; Cell, vol. 115, 209-216, Oct. 17, 2003.

Miyagishi, Makoto, et al; Comparison of the Suppressive Effects of Antisense Oligonucleotides and siRNAs Directed Against the Same Targets in Mammalian Cells; Antisense and Nucleic Acid Drug Development 13:1-7 (2003).

Reynolds, Angela, et al; Rational siRNA design for RNA interference; Nature Biotechnology; vol. 22, No. 3, Mar. 2004.

Scherr, Michaela, et al.; Detection of Antisense and Ribozyme Accessible Sites on Native mRNAs: Application to NCOA3 mRNA; Molecular Therapy, vol. 4, No. 5, Nov. 2001.

Scherr, Michaela, et al.; Oligonucleotide Scanning of Native mRNAs in Extracts Predicts Intracellular Ribozyme Efficiency: Ribozyme-Mediated Reduction of the Murine DNA Methyltransferase; Molecular Therapy, vol. 2, No. 1, Jul. 2000.

Scherr, Michaela, et al.; Rapid determination and quantitation of the accessibility to native RNAs by antisense oligodeoxynucleotides in murine cell extracts; Nucleic Acids Research, 1998, vol. 26, No. 22; 5079-5085.

Schubert, Steffen, et al.; Local RNA Target Structure Influences siRNA Efficacy: Systematic Analysis of Intentionally Designed Binding Regions; J. Mol. Biol. (2005) 348, 883-893.

* cited by examiner

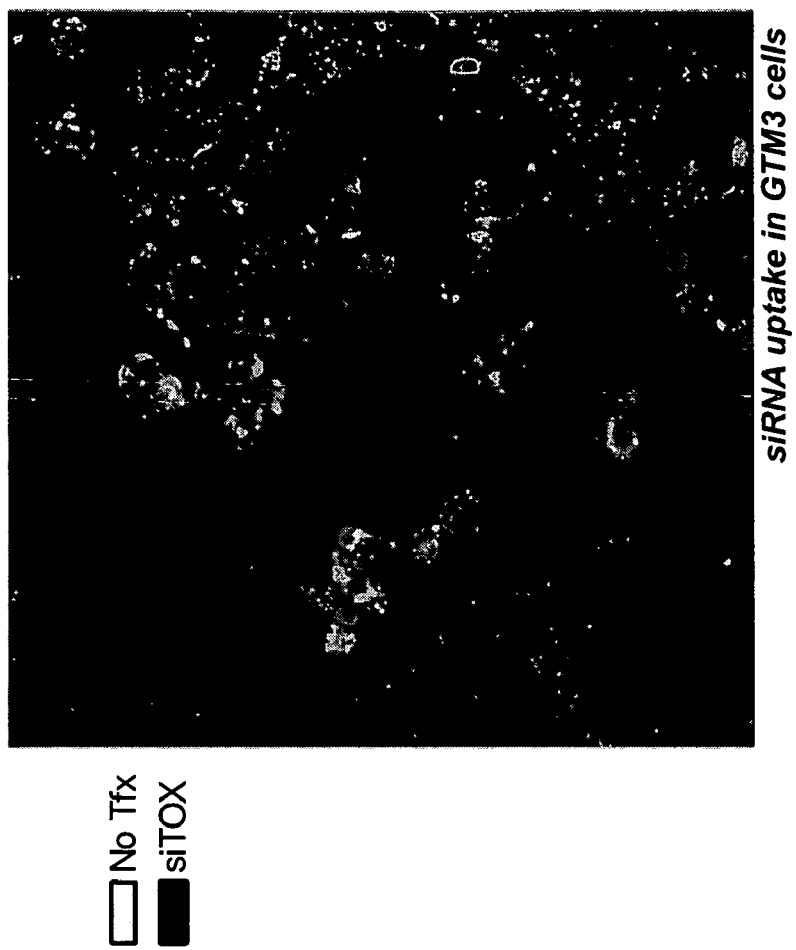
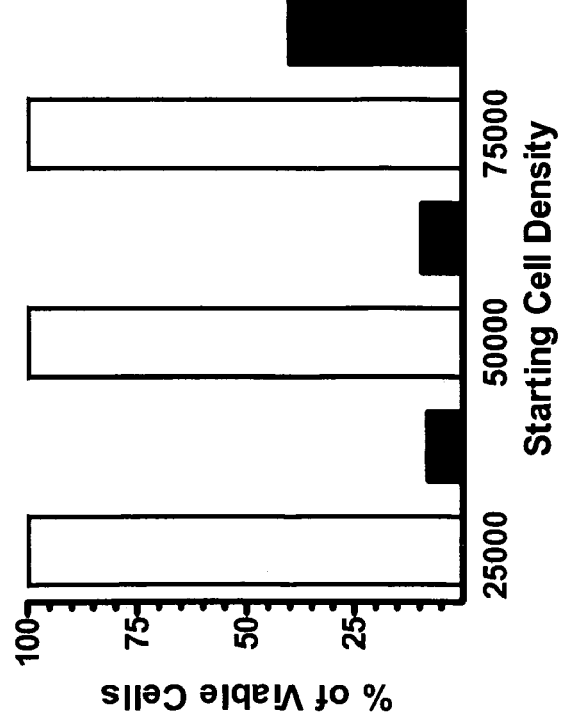
FIG. 1A
FIG. 1B

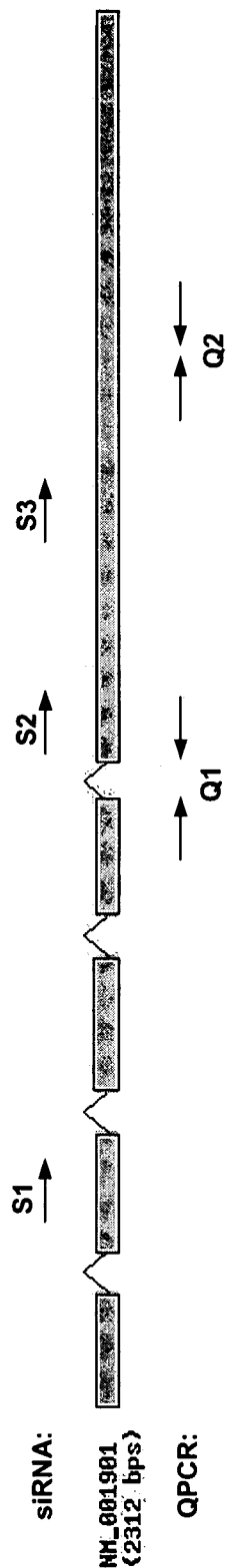
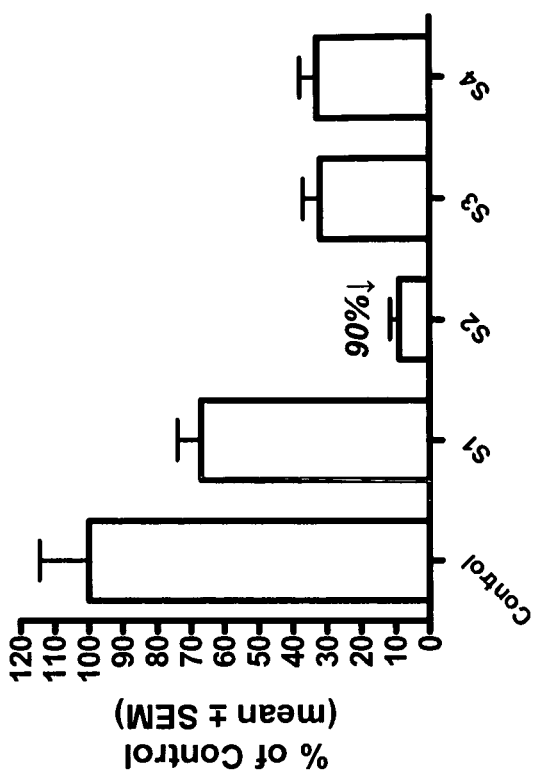
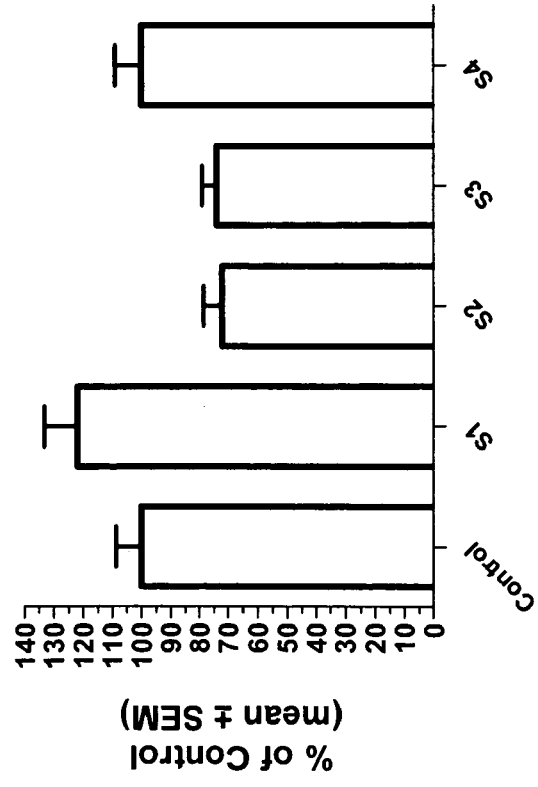
FIG. 2A
FIG. 2B
FIG. 2C

SEQUENCE LISTING

```
<160> NUMBER OF SEQ ID NOS: 36

<210> SEQ ID NO 1
<211> LENGTH: 2312
<212> TYPE: DNA
<213> ORGANISM: Homo sapiens

<400> SEQUENCE: 1
tccagtgacg gagccgcccg gccgacagcc ccgagacgac agcccggcgc gtcccggtcc      60
ccacctccga ccaccgccag cgctccaggc cccgcgctcc ccgctcgccg ccaccgcgcc     120
ctccgctccg cccgcagtgc caaccatgac cgccgccagt atgggccccg tccgcgtcgc     180
cttcgtggtc ctcctcgccc tctgcagccg gccggccgtc ggccagaact gcagcgggcc     240
gtgccggtgc ccggacgagc cggcgccgcg ctgcccggcg ggcgtgagcc tcgtgctgga     300
cggctgcggc tgctgccgcg tctgcgccaa gcagctgggc gagctgtgca ccgagcgcga     360 ccccctgcgac ccgcacaagg gcctcttctg tgacttcggc tccccggcca accgcaagat     420
cggcgtgtgc accgccaaag atggtgctcc ctgcatcttc ggtggtacgg tgtaccgcag     480
cggagagtcc ttccagagca gctgcaagta ccagtgcacg tgcctggacg gggcggtggg     540
ctgcatgccc ctgtgcagca tggacgttcg tctgcccagc cctgactgcc ccttcccgag     600
gagggtcaag ctgcccggga aatgctgcga ggagtgggtg tgtgacgagc caaggacca     660 aaccgtggtt gggcctgccc tcgcggctta ccgactggaa gacacgtttg gcccagaccc     720
aactatgatt agagccaact gcctggtcca gaccacagag tggagcgcct gttccaagac     780
ctgtgggatg ggcatctcca cccgggttac caatgacaac gcctcctgca ggctagagaa     840
gcagagccgc ctgtgcatgg tcaggccttg cgaagctgac ctggaagaga acattaagaa     900
gggcaaaaag tgcatccgta ctcccaaaat ctccaagcct atcaagtttg agctttctgg     960
ctgcaccagc atgaagacat accgagctaa attctgtgga gtatgtaccg acggccgatg    1020
ctgcaccccc cacagaacca ccaccctgcc ggtggagttc aagtgccctg acggcgaggt    1080
```

```
catgaagaag aacatgatgt tcatcaagac ctgtgcctgc cattacaact gtcccggaga    1140
caatgacatc tttgaatcgc tgtactacag gaagatgtac ggagacatgg catgaagcca    1200
gagagtgaga gacattaact cattagactg gaacttgaac tgattcacat ctcattttc     1260 cgtaaaaatg atttcagtag cacaagttat ttaaatctgt ttttctaact gggggaaaag    1320
attcccaccc aattcaaaac attgtgccat gtcaaacaaa tagtctatct tccccagaca    1380
ctggtttgaa gaatgttaag acttgacagt ggaactacat tagtacacag caccagaatg    1440
tatattaagg tgtggcttta ggagcagtgg gagggtacca gcagaaaggt tagtatcatc     1500
agatagctct tatacgagta atatgcctgc tatttgaagt gtaattgaga aggaaaattt    1560
tagcgtgctc actgacctgc ctgtagcccc agtgacagct aggatgtgca ttctccagcc    1620
atcaagagac tgagtcaagt tgttccttaa gtcagaacag cagactcagc tctgacattc    1680
tgattcgaat gacactgttc aggaatcgga atcctgtcga ttagactgga cagcttgtgg    1740
caagtgaatt tcctgtaaca agccagattt tttaaaattt atattgtaaa tattgtgtgt    1800
gtgtgtgtgt gtgtatatat atatatatat gtacagttat ctaagttaat ttaaagttgt    1860
ttgtgccttt ttatttttgt ttttaatgct ttgatatttc aatgttagcc tcaatttctg    1920
aacaccatag gtagaatgta aagcttgtct gatcgttcaa agcatgaaat ggatacttat    1980
atggaaattc tctcagatag aatgacagtc cgtcaaaaca gattgtttgc aaagggagg     2040 catcagtgtc cttggcaggc tgatttctag gtaggaaatg tggtagctca cgctcacttt    2100
taatgaacaa atggccttta ttaaaaactg agtgactcta tatagctgat cagttttttc    2160
acctggaagc atttgtttct actttgatat gactgttttt cggacagttt atttgttgag    2220
agtgtgacca aaagttacat gtttgcacct ttctagttga aaataaagta tattttttct    2280
aaaaaaaaaa aaaaacgaca gcaacggaat tc                                  2312

<210> SEQ ID NO 2
<211> LENGTH: 19
<212> TYPE: DNA
<213> ORGANISM: Artificial Sequence
<220> FEATURE:
<223> OTHER INFORMATION: TARGETING SEQUENCE

<400> SEQUENCE: 2
gggcctcttc tgtgacttc                                                 19

<210> SEQ ID NO 3
<211> LENGTH: 19
<212> TYPE: DNA
<213> ORGANISM: Artificial Sequence
<220> FEATURE:
<223> OTHER INFORMATION: Targeting Sequence

<400> SEQUENCE: 3
ccgactggaa gacacgttt                                                 19

<210> SEQ ID NO 4
<211> LENGTH: 19
<212> TYPE: DNA
<213> ORGANISM: Artificial Sequence
<220> FEATURE:
<223> OTHER INFORMATION: Targeting Sequence

<400> SEQUENCE: 4
cccgggttac caatgacaa                                                 19
```

<210> SEQ ID NO 5
<211> LENGTH: 25
<212> TYPE: DNA
<213> ORGANISM: Artificial Sequence
<220> FEATURE:
<223> OTHER INFORMATION: Targeting Sequence

<400> SEQUENCE: 5
tccaagccta tcaagtttga gcttt                                          25

<210> SEQ ID NO 6
<211> LENGTH: 25
<212> TYPE: DNA
<213> ORGANISM: Artificial Sequence
<220> FEATURE:
<223> OTHER INFORMATION: Targeting Sequence

<400> SEQUENCE: 6
tccaagccta tcaagtttga gcttt                                          25

<210> SEQ ID NO 7
<211> LENGTH: 19
<212> TYPE: DNA
<213> ORGANISM: Artificial Sequence
<220> FEATURE:
<223> OTHER INFORMATION: Targeting Sequence

<400> SEQUENCE: 7
gcctatcaag tttgagctt                                                 19

<210> SEQ ID NO 8
<211> LENGTH: 25
<212> TYPE: DNA
<213> ORGANISM: Artificial Sequence
<220> FEATURE:
<223> OTHER INFORMATION: Targeting Sequence

<400> SEQUENCE: 8
gcatgaagac ataccgagct aaatt                                          25

<210> SEQ ID NO 9
<211> LENGTH: 19
<212> TYPE: DNA
<213> ORGANISM: Artificial Sequence
<220> FEATURE:
<223> OTHER INFORMATION: Targeting Sequence

<400> SEQUENCE: 9
gctaaattct gtggagtat                                                 19

<210> SEQ ID NO 10
<211> LENGTH: 25
<212> TYPE: DNA
<213> ORGANISM: Artificial Sequence
<220> FEATURE:
<223> OTHER INFORMATION: Targeting Sequence

<400> SEQUENCE: 10
gccattacaa ctgtcccgga gacaa                                          25

<210> SEQ ID NO 11
<211> LENGTH: 19
<212> TYPE: DNA
<213> ORGANISM: Artificial Sequence
<220> FEATURE:
<223> OTHER INFORMATION: Targeting Sequence

```
<400> SEQUENCE: 11
ggaagatgta cggagacat                                               19

<210> SEQ ID NO 12
<211> LENGTH: 25
<212> TYPE: DNA
<213> ORGANISM: Artificial Sequence
<220> FEATURE:
<223> OTHER INFORMATION: Targeting Sequence

<400> SEQUENCE: 12
gagagtgaga gacattaact catta                                        25

<210> SEQ ID NO 13
<211> LENGTH: 25
<212> TYPE: DNA
<213> ORGANISM: Artificial Sequence
<220> FEATURE:
<223> OTHER INFORMATION: Targeting Sequence

<400> SEQUENCE: 13
gccatgtcaa acaaatagtc tatct                                        25

<210> SEQ ID NO 14
<211> LENGTH: 19
<212> TYPE: DNA
<213> ORGANISM: Artificial Sequence
<220> FEATURE:
<223> OTHER INFORMATION: Targeting Sequence

<400> SEQUENCE: 14
gggtaccagc agaaaggtt                                               19

<210> SEQ ID NO 15
<211> LENGTH: 19
<212> TYPE: DNA
<213> ORGANISM: Artificial
<220> FEATURE:
<223> OTHER INFORMATION: Targeting Sequence

<400> SEQUENCE: 15
ccagcagaaa ggttagtat                                               19

<210> SEQ ID NO 16
<211> LENGTH: 19
<212> TYPE: DNA
<213> ORGANISM: Artificial Sequence
<220> FEATURE:
<223> OTHER INFORMATION: Targeting Sequence

<400> SEQUENCE: 16
gcagaaaggt tagtatcat                                               19

<210> SEQ ID NO 17
<211> LENGTH: 25
<212> TYPE: DNA
<213> ORGANISM: Artificial Sequence
<220> FEATURE:
<223> OTHER INFORMATION: Targeting Sequence

<400> SEQUENCE: 17
gcagaaaggt tagtatcatc agata                                        25

<210> SEQ ID NO 18
```

```
<211> LENGTH: 19
<212> TYPE: DNA
<213> ORGANISM: Artificial Sequence
<220> FEATURE:
<223> OTHER INFORMATION: Targeting Sequence

<400> SEQUENCE: 18
ggttagtatc atcagatag                                                        19

<210> SEQ ID NO 19
<211> LENGTH: 25
<212> TYPE: DNA
<213> ORGANISM: Artificial Sequence
<220> FEATURE:
<223> OTHER INFORMATION: Targeting Sequence

<400> SEQUENCE: 19
ggttagtatc atcagatagc tctta                                                 25

<210> SEQ ID NO 20
<211> LENGTH: 25
<212> TYPE: DNA
<213> ORGANISM: Artificial Sequence
<220> FEATURE:
<223> OTHER INFORMATION: Targeting Sequence

<400> SEQUENCE: 20
gagactgagt caagttgttc cttaa                                                 25

<210> SEQ ID NO 21
<211> LENGTH: 19
<212> TYPE: DNA
<213> ORGANISM: Artificial Sequence
<220> FEATURE:
<223> OTHER INFORMATION: Targeting Sequence

<400> SEQUENCE: 21
gcagactcag ctctgacat                                                        19

<210> SEQ ID NO 22
<211> LENGTH: 25
<212> TYPE: DNA
<213> ORGANISM: Artificial Sequence
<220> FEATURE:
<223> OTHER INFORMATION: Targeting Sequence

<400> SEQUENCE: 22
tcagctctga cattctgatt cgaat                                                 25

<210> SEQ ID NO 23
<211> LENGTH: 25
<212> TYPE: DNA
<213> ORGANISM: Artificial Sequence
<220> FEATURE:
<223> OTHER INFORMATION: Targeting Sequence

<400> SEQUENCE: 23
tcctgtcgat tagactggac agctt                                                 25

<210> SEQ ID NO 24
<211> LENGTH: 19
<212> TYPE: DNA
<213> ORGANISM: Artificial Sequence
<220> FEATURE:
<223> OTHER INFORMATION: Targeting Sequence

<400> SEQUENCE: 24
```

```
gcttgtggca agtgaatttt                                                    19

<210> SEQ ID NO 25
<211> LENGTH: 21
<212> TYPE: RNA
<213> ORGANISM: Artificial Sequence
<220> FEATURE:
<223> OTHER INFORMATION: Sense Strand

<400> SEQUENCE: 25
gguuaguauc aucagauagu u                                                  21

<210> SEQ ID NO 26
<211> LENGTH: 21
<212> TYPE: RNA
<213> ORGANISM: Artificial Sequence
<220> FEATURE:
<223> OTHER INFORMATION: Antisense Strand

<400> SEQUENCE: 26
cuaucugaug auacuaaccu u                                                  21

<210> SEQ ID NO 27
<211> LENGTH: 21
<212> TYPE: DNA
<213> ORGANISM: Artificial Sequence
<220> FEATURE:
<223> OTHER INFORMATION: Sense Strand with 3'TT
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 27
gguuaguauc aucagauagt t                                                  21

<210> SEQ ID NO 28
<211> LENGTH: 21
<212> TYPE: DNA
<213> ORGANISM: Artificial Sequence
<220> FEATURE:
<223> OTHER INFORMATION: Antisense Strand with 3'TT
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 28
cuaucugaug auacuaacct t                                                  21

<210> SEQ ID NO 29
<211> LENGTH: 51
<212> TYPE: DNA
<213> ORGANISM: Artificial Sequence
<220> FEATURE:
<223> OTHER INFORMATION: Hairpin Duplex With Loop
<220> FEATURE:
<221> NAME/KEY: misc_RNA
<222> LOCATION: (1)..(21)
<223> OTHER INFORMATION: ribonucleotides
<220> FEATURE:
```

```
<221> NAME/KEY: misc_feature
<222> LOCATION: (22)..(30)
<223> OTHER INFORMATION: any, A, T/U, C, G
<220> FEATURE:
<221> NAME/KEY: misc_feature
<222> LOCATION: (31)..(51)
<223> OTHER INFORMATION: ribonucleotides

<400> SEQUENCE: 29
gguuaguauc aucagauagu unnnnnnnnn cuaucugaug auacuaaccu u        51

<210> SEQ ID NO 30
<211> LENGTH: 21
<212> TYPE: DNA
<213> ORGANISM: Artificial Sequence
<220> FEATURE:
<223> OTHER INFORMATION: Sense Strand with 3'TT
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 30
gggccucuuc ugugacuuct t                                         21

<210> SEQ ID NO 31
<211> LENGTH: 21
<212> TYPE: DNA
<213> ORGANISM: Artificial Sequence
<220> FEATURE:
<223> OTHER INFORMATION: Antisense Strand with 3'TT
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 31
gaagucacag aagaggcccT t                                         21

<210> SEQ ID NO 32
<211> LENGTH: 21
<212> TYPE: DNA
<213> ORGANISM: Artificial Sequence
<220> FEATURE:
<223> OTHER INFORMATION: Sense Strand with 3'TT
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 32
gggcaaaaag ugcauccgut t                                         21

<210> SEQ ID NO 33
<211> LENGTH: 21
<212> TYPE: DNA
<213> ORGANISM: Artificial
<220> FEATURE:
<223> OTHER INFORMATION: Antisense Strand with 3'TT
```

```
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 33
acggaugcac uuuuugcccu t                                             21

<210> SEQ ID NO 34
<211> LENGTH: 23
<212> TYPE: DNA
<213> ORGANISM: Artificial Sequence
<220> FEATURE:
<223> OTHER INFORMATION: Probe/Primer Sequence

<400> SEQUENCE: 34
cagctctgac attctgattc gaa                                           23

<210> SEQ ID NO 35
<211> LENGTH: 20
<212> TYPE: DNA
<213> ORGANISM: Artificial Sequence
<220> FEATURE:
<223> OTHER INFORMATION: Probe/Primer Sequence

<400> SEQUENCE: 35
tgccacaagc tgtccagtct                                               20

<210> SEQ ID NO 36
<211> LENGTH: 30
<212> TYPE: DNA
<213> ORGANISM: Artificial Sequence
<220> FEATURE:
<223> OTHER INFORMATION: Probe/Primer Sequence

<400> SEQUENCE: 36
aatcgacagg attccgattc ctgaacagtg                                    30
```

RNAI INHIBITION OF CTGF FOR TREATMENT OF OCULAR DISORDERS

The present application claims the benefit of U.S. Provisional Patent Application Ser. No. 60/638,705 filed Dec. 23, 2004, the text of which is specifically incorporated by reference herein.

FIELD OF THE INVENTION

The present invention relates to the field of interfering RNA compositions for inhibition of expression of connective tissue growth factor (CTGF) in ocular disorders.

BACKGROUND OF THE INVENTION

Most ocular disorders are associated with cellular processes including cell proliferation, survival, migration, differentiation, and angiogenesis. CTGF is a secreted cytokine and a central mediator in these cellular processes. In particular, CTGF is known to increase extracellular matrix production primarily via increased deposition of collagen I and fibronectin. Overexpression of CTGF has been implicated as a major causative factor in conditions such as scleroderma, fibroproliferative diseases, and scarring in which there is an overaccumulation of extracellular matrix components.

An overaccumulation of extracellular matrix materials in the region of the trabecular meshwork (TM) is a hallmark of many forms of glaucoma; such increases are believed to lead to increased resistance to aqueous outflow and, therefore, elevated intraocular pressures. International Patent Application No. PCT/US2003/012521 to Fleenor et al. published Nov. 13, 2003 as WO 03/092584 and assigned to Alcon, Inc. describes the elevated presence of CTGF mRNA in glaucomatous TM cells vs. normal TM cells. Thus, it is believed that CTGF plays a role in extracellular matrix production by the trabecular meshwork cells.

Macular degeneration is the loss of photoreceptors in the portion of the central retina, termed the macula, responsible for high-acuity vision. Degeneration of the macula is associated with abnormal deposition of extracellular matrix components in the membrane between the retinal pigment epithelium and the vascular choroid. This debris-like material is termed drusen. Drusen is observed using a funduscopic eye examination. Normal eyes may have maculas free of drusen, yet drusen may be abundant in the retinal periphery. The presence of soft drusen in the macula, in the absence of any loss of macular vision, is considered an early stage of AMD.

Choroidal neovascularization commonly occurs in macular degeneration in addition to other ocular disorders and is associated with proliferation of choroidal endothelial cells, overproduction of extracellular matrix, and formation of a fibrovascular subretinal membrane. Retinal pigment epithelium cell proliferation and production of angiogenic factors appears to effect choroidal neovascularization.

Diabetic retinopathy is an ocular disorder that develops in diabetes due to thickening of capillary basement membranes and lack of contact between pericytes and endothelial cells of the capillaries. Loss of pericytes increases leakage of the capillaries and leads to breakdown of the blood-retina barrier.

Proliferative vitreoretinopathy is associated with cellular proliferation of cellular and fibrotic membranes within the vitreous membranes and on the surfaces of the retina. Retinal pigment epithelium cell proliferation and migration is common with this ocular disorder. The membranes associated with proliferative vitreoretinopathy contain extracellular matrix components such as collagen types I, II, and IV and fibronectin, and become progressively fibrotic.

Wound healing disorders may lead to severe ocular tissue damage via activation of inflammatory cells, release of growth factors and cytokines, proliferation and differentiation of ocular cells, increased capillary permeability, alterations in basement membrane matrix composition, increased deposition of extracellular matrix, fibrosis, neovascularization, and tissue remodeling.

Overexpression of CTGF therefore has been implicated as a major causative factor in these ocular disorders. Current therapies do not directly address the pathogenic mechanism of these disorders.

SUMMARY OF THE INVENTION

The present invention is directed to interfering RNAs that target CTGF mRNA and thereby interfere with CTGF mRNA expression. The interfering RNAs of the invention are useful for treating CTGF-related ocular disorders such as glaucoma, macular degeneration, diabetic retinopathy, choroidal neovascularization, proliferative vitreoretinopathy and aberrant wound healing.

An embodiment of the present invention provides a method of attenuating expression of connective tissue growth factor mRNA in an eye of a subject. The method comprises administering to the eye of the subject a composition comprising an effective amount of interfering RNA such as double-stranded (ds) siRNA or single-stranded (ss) siRNA having a length of 19 to 49 nucleotides and a pharmaceutically acceptable carrier.

The double stranded siRNA comprises a sense nucleotide sequence, an antisense nucleotide sequence and a region of at least near-perfect contiguous complementarity of at least 19 nucleotides. Further, the antisense sequence hybridizes under physiological conditions to a portion of mRNA corresponding to SEQ ID NO:1 (the sense strand sequence of DNA for connective tissue growth factor for humans, GenBank reference no. NM_001901), and has a region of at least near-perfect contiguous complementarity of at least 19 nucleotides with the hybridizing portion of mRNA corresponding to SEQ ID NO:1. The administration of such a composition attenuates the expression of connective tissue growth factor mRNA of the eye of the subject.

The single-stranded siRNA has a length of 19 to 49 nucleotides, hybridizes under physiological conditions to a portion of mRNA corresponding to SEQ ID NO:1 beginning at nucleotide 379, 691, 801, 901, 932, 937, 969, 986, 1119, 1170, 1201, 1346, 1473, 1478, 1481, 1488, 1626, 1660, or 1666, and has a region of at least near-perfect complementarity with the hybridizing portion of mRNA corresponding to SEQ ID NO:1.

In an embodiment of the invention, the antisense sequence of a double-stranded interfering RNA is designed to target a nucleotide sequence of mRNA corresponding to SEQ ID NO:1 beginning at or comprising nucleotide 379, 691, 801, 901, 932, 937, 969, 986, 1119, 1170, 1201, 1346, 1473, 1478, 1481, 1488, 1626, 1660, or 1666.

A further embodiment of the invention is a method of treating a connective tissue growth factor-associated ocular disorder in a subject in need thereof. The method comprises administering to the eye of the subject a composition comprising an effective amount of interfering RNA having a length of 19 to 49 nucleotides and a pharmaceutically acceptable carrier, the interfering RNA comprising a sense nucleotide sequence, an antisense nucleotide sequence, and a region of at least near-perfect contiguous complementarity of at least 19 nucleotides. The antisense sequence hybridizes under physiological conditions to a portion of mRNA corresponding to SEQ ID NO:1, and has a region of at least near-perfect contiguous complementarity of at least 19 nucleotides with the hybridizing portion of mRNA corresponding to SEQ ID NO:1. The connective tissue growth factor-associated ocular disorder is treated thereby.

BRIEF DESCRIPTION OF THE DRAWINGS

FIG. 1A shows SITOX™ data demonstrating that transfection efficiency of trabecular meshwork cells was not rate-limiting when taken together with data of FIG. 1B. GTM3 cells were transfected with SITOX™ (Dharmacon) transfection control. After 24 hr, trypan blue exclusion was used to determine the number of viable cells remaining in the SITOX™ culture, which reflects the relative transfection efficiency. Open bars: no transfection; Solid bars: with SITOX™.

FIG. 1B shows a SIGLO™ image of siRNA uptake in GTM3 cells demonstrating that transfection efficiency was not rate-limiting when taken together with data of FIG. 1A. GTM3 cells were transfected with SIGLO™ siRNA (Dharmacon) using LIPOFECTAMINE 2000™. SIGLO™ siRNA uptake was determined after 24 hr using fluorescence microscopy (red irregular shapes). Individual cell nuclei were identified by DAPI (4',6-diamidino-2-phenylindole), a stain for double stranded DNA (blue round areas). As the data of FIG. 1A and the image of FIG. 1B show, nearly all cells were either dead (SITOX™) or fluorescent (SIGLO™).

FIG. 2A is a schematic showing the CTGF gene exon (boxes) and intron (lines) structure and location of siRNAs S1, S2, and S3 and QPCR primer/probe sets Q1 and Q2 in relation to the GenBank CTGF sequence NM_001901, the sequence of which is provided as SEQ ID NO:1. The sequences of the siRNAs and primer/probe sets are provided in Example 1.

FIG. 2B shows QPCR amplification of CTGF mRNA using the exon 5 primer/probe set Q2. Using the S1 and S4 siRNAs, no significant knock-down of the CTGF mRNA levels was detected.

FIG. 2C shows QPCR amplification of CTGF mRNA using the exon 4/5 spanning primer/probe set Q1. Knock-down of CTGF mRNA was observed by each of the siRNAs and an ~90% knock-down was observed with the S2 siRNA.

DETAILED DESCRIPTION OF THE INVENTION

Figure 3:
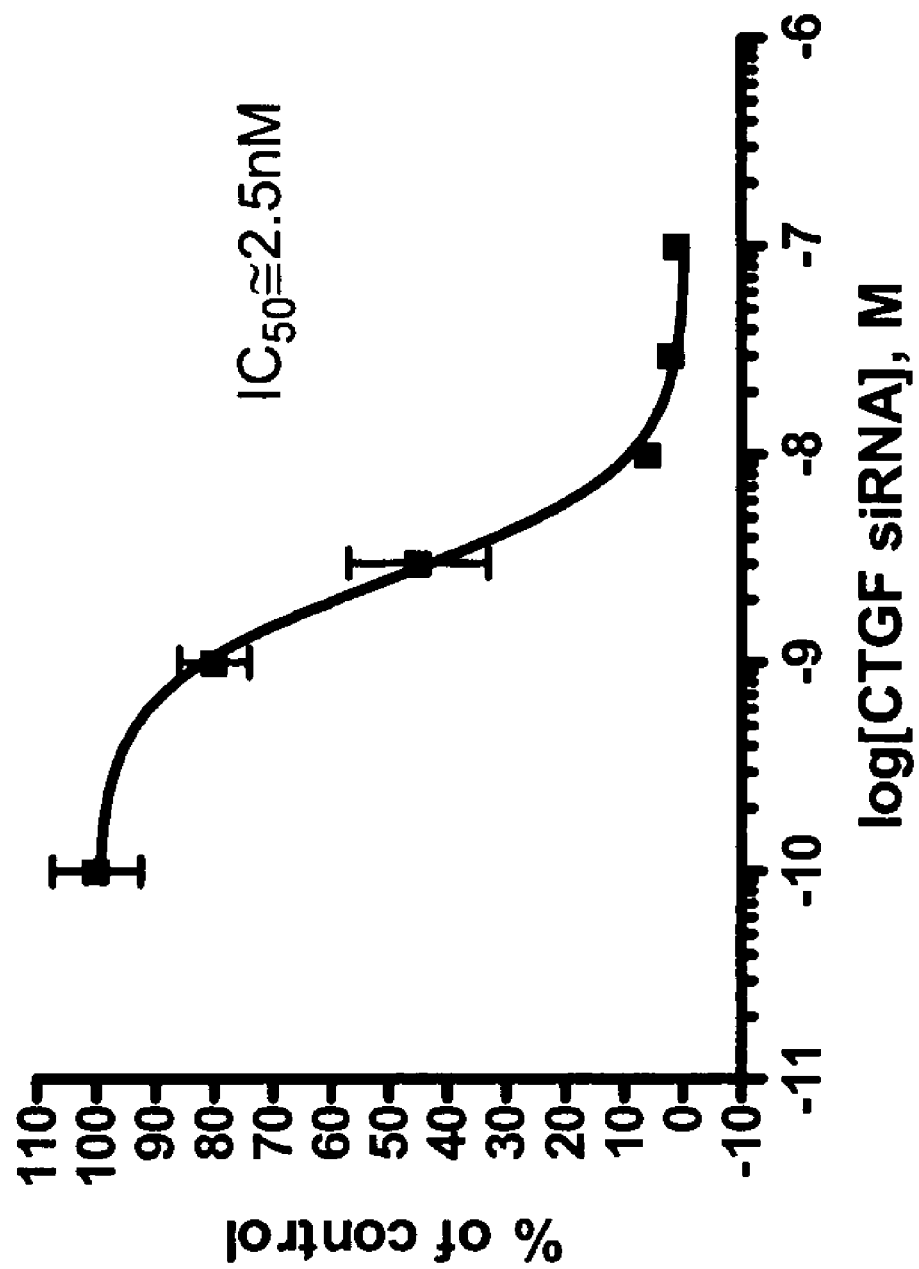
FIG. 3 shows a titration study in which various concentrations of the S2 siRNA were tested for efficacy of knock-down of CTGF mRNA levels. CTGF mRNA knock-down was assessed by QPCR amplification using primer/probe set Q1. An $IC_{50}$ of ~2.5nM was observed in GTM3 cells after 24 hour treatment with 0, 1, 3, 10, 30, and 100 nM S2 siRNA as described in Example 1.

RNA interference, termed "RNAi," is a method for reducing the expression of a target gene that is effected by small single- or double-stranded RNA molecules. Interfering RNAs include small interfering RNAs, either double-stranded or single-stranded (ds siRNAs or ss siRNAs), microRNAs (miRNAs), small hairpin RNAs (shRNAs), and others. While not wanting to be bound by theory, RNA interference appears to occur in vivo with the cleavage of dsRNA precursors into small RNAs of about 20 to 25 nucleotides in length. Cleavage is accomplished by RNaseIII-RNA helicase Dicer. The "sense" strand of an siRNA, i.e., the strand that has exactly the same sequence as a target mRNA sequence, is removed, leaving the 'antisense" strand which is complementary to the target mRNA to function in reducing expression of the mRNA. The antisense strand of the siRNA appears to guide a protein complex known as RISC (RNA-induced silencing complex) to the mRNA, which complex then cleaves the mRNA by the Argonaute protein of the RISC, thereby reducing protein production by that mRNA. Interfering RNAs are catalytic and reduction in expression of mRNA can be achieved with substoichiometric amounts of interfering RNAs in relation to mRNA. Reduction in mRNA expression may also occur via transcriptional and translational mechanisms.

The present invention relates to the use of interfering RNA for inhibition of expression of connective tissue growth factor (CTGF) in ocular disorders. According to the present invention, tissues of the eye, in particular, trabecular meshwork cells of the eye, carry out siRNA silencing, and exogenously provided siRNAs effect silencing. Further, aspects of the present invention have determined that, when using a PCR-based approach to determine the efficacy of siRNA knock-down, the PCR amplification primers should be designed to encompass the siRNA targeting sequence to accurately measure silencing.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid" includes the terms "oligonucleotide" and "polynucleotide" and can refer to a single stranded molecule or a double stranded molecule. A double stranded molecule is formed by Watson-Crick base pairing between A and T bases, C and G bases, and A and U bases. The strands of a double stranded molecule may have partial, substantial or full complementarity to each other and will form a duplex hybrid, the strength of bonding of which is dependent upon the nature and degree of complementarity of the sequence of bases. A mRNA sequence is readily determined by knowing the sense or antisense strand sequence of DNA encoding therefore. For example, SEQ ID NO:1 provides the sense strand sequence of DNA corresponding to the mRNA for connective tissue growth factor. The sequence of mRNA is identical to the sequence of the sense strand of DNA with the "T" bases replaced with "U" residues. Therefore, the mRNA sequence of connective tissue growth factor is known from SEQ ID NO:1.

Connective tissue growth factor mRNA. The GenBank database of the National Center for Biotechnology Information at ncbi.nlm.nih.gov provides the corresponding DNA sequence for the messenger RNA of human connective tissue growth factor as reference no. NM_001 901, provided below as SEQ ID NO:1. The coding sequence for connective tissue growth factor is from nucleotides 146-1195.

SEQ ID NO:1:

```
   1 tccagtgacg gagccgcccg gccgacagcc ccgagacgac agcccggcgc gtcccggtcc
  61 ccacctccga ccaccgccag cgctccaggc cccgcgctcc ccgctcgccg ccaccgcgcc
 121 ctccgctccg cccgcagtgc caaccatgac cgccgccagt atgggccccg tccgcgtcgc
 181 cttcgtggtc ctcctcgccc tctgcagccg gccggccgtc ggccagaact gcagcgggcc
 241 gtgccggtgc ccggacgagc cggcgccgcg ctgcccggcg ggcgtgagcc tcgtgctgga
 301 cggctgcggc tgctgccgcg tctgcgccaa gcagctgggc gagctgtgca ccgagcgcga
 361 cccctgcgac ccgcacaagg gcctcttctg tgacttcggc tccccggcca accgcaagat
 421 cggcgtgtgc accgccaaag atggtgctcc ctgcatcttc ggtggtacgg tgtaccgcag
 481 cggagagtcc ttccagagca gctgcaagta ccagtgcacg tgcctggacg ggcggtggg
 541 ctgcatgccc ctgtgcagca tggacgttcg tctgcccagc cctgactgcc ccttcccgag
 601 gagggtcaag ctgcccggga atgctgcgga ggagtgggtg tgtgacgagc caaggacca
 661 aaccgtggtt gggcctgccc tcgcggctta ccgactggaa gacacgtttg cccagaccc
 721 aactatgatt agagccaact gcctggtcca gaccacagag tggagcgcct gttccaagac
 781 ctgtgggatg ggcatctcca cccgggttac caatgacaac gcctcctgca ggctagagaa
 841 gcagagccgc ctgtgcatgg tcaggccttg cgaagctgac ctggaagaga acattaagaa
 901 gggcaaaaag tgcatccgta ctcccaaaat ctccaagcct atcaagtttg agctttctgg
 961 ctgcaccagc atgaagacat accgagctaa attctgtgga gtatgtaccg acggccgatg
1021 ctgcacccc cacagaacca ccaccctgcc ggtggagttc aagtgccctg acggcgaggt
1081 catgaagaag aacatgatgt tcatcaagac ctgtgcctgc cattacaact gtcccggaga
1141 caatgacatc tttgaatcgc tgtactacag gaagatgtac ggagacatgg catgaagcca
1201 gagagtgaga gacattaact cattagactg gaacttgaac tgattcacat ctcattttc
1261 cgtaaaaatg atttcagtag cacaagttat ttaaatctgt ttttctaact ggggaaaag
1321 attcccaccc aattcaaaac attgtgccat gtcaaacaaa tagtctatct tccccagaca
1381 ctggtttgaa gaatgttaag acttgacagt ggaactacat tagtacacag caccagaatg
1441 tatattaagg tgtggcttta ggagcagtgg gagggtacca gcagaaaggt tagtatcatc
1501 agatagctct tatacgagta atatgcctgc tatttgaagt gtaattgaga aggaaaattt
1561 tagcgtgctc actgacctgc ctgtagcccc agtgacagct aggatgtgca ttctccagcc
1621 atcaagagac tgagtcaagt tgttccttaa gtcagaacag cagactcagc tctgacattc
1681 tgattcgaat gacactgttc aggaatcgga atcctgtcga ttagactgga cagcttgtgg
1741 caagtgaatt tcctgtaaca agccagattt tttaaaattt atattgtaaa tattgtgtgt
1801 gtgtgtgtgt gtgtatatat atatatatat gtacagttat ctaagttaat ttaaagttgt
1861 ttgtgccttt ttattttgt ttaatgct ttgatattc aatgttagcc tcaatttctg
1921 aacaccatag gtagaatgta aagcttgtct gatcgttcaa agcatgaaat ggatacttat
1981 atggaaattc tctcagatag aatgacagtc cgtcaaaaca gattgtttgc aaaggggagg
2041 catcagtgtc cttggcaggc tgatttctag gtaggaaatg tggtagctca cgctcacttt
2101 taatgaacaa atggccttta ttaaaaactg agtgactcta tatagctgat cagttttttc
2161 acctggaagc atttgtttct actttgatat gactgttttt cggacagttt atttgttgag
2221 agtgtgacca aaagttacat gtttgcacct ttcagttgaa aaataaagta tattttttct
2281 aaaaaaaaaa aaaacgaca gcaacggaat tc.
```

Equivalents of the above cited CTGF mRNA sequence are alternative splice forms, allelic forms, or a cognate thereof. A cognate is a connective tissue growth factor mRNA from another mammalian species that is homologous to SEQ ID NO:1. CTGF nucleic acid sequences related to SEQ ID NO:1 are those having GenBank accession numbers AK092280, AK125220, AY395801, AY550024, BT019794, BT019795, CR541759, M92934, U14750, and X78947, and the sequence of SEQ ID NO:1 of U.S. Pat. No. 5,585,270, incorporated by reference herein.

Attenuating expression of an mRNA: The phrase, "attenuating expression of an mRNA," as used herein, means administering an amount of interfering RNA to effect a reduction of the full mRNA transcript levels of a target gene in a cell, thereby decreasing translation of the mRNA into protein as compared to a control RNA having a scrambled sequence. The reduction in expression of the mRNA is commonly referred to as "knock-down" of mRNA. Knock-down of expression of an amount of between and including an amount of 50% and 100% is contemplated by embodiments herein. However, it is not necessary that such knock-down levels be achieved for purposes of the present invention. Further, two sets of interfering RNAs may be mildly effective at knock-down individually, however, when administered together may be significantly more effective. In one embodiment, an individual ds siRNA is effective at knock-down at an amount of at least up to 70%. In another embodiment, two or more ds siRNAs are together effective at knock-down at an amount of at least up to 70%.

Knock-down is commonly measured by determining the mRNA levels by Quantitative Polymerase Chain Reaction (QPCR) amplification or by determining protein levels by Western Blot or enzyme linked immunosorbent assay (ELISA). Analyzing the protein level provides an assessment of both mRNA degradation by the RNA Induced Silencing Complex (RISC) as well as translation inhibition. Further techniques for measuring knock-down include RNA solution hybridization, nuclease protection, Northern hybridization, reverse transcription, gene expression monitoring with a microarray, antibody binding, radioimmunoassay, and fluorescence activated cell analysis. A further method of measurement includes overexpressing TGFβ2 which induces CTGF, adding back CTGF siRNA, and then measuring CTGF mRNA/protein knockdown by any of the above-cited methods.

Inhibition of CTGF is also inferred in a human or mammal by observing an improvement in an ocular disorder. For example, in age related macular degeneration a slowing or reversal of vision loss indicates an inhibition of CTGF and silencing of CTGF mRNA in glaucoma patients leads to lowered intraocular pressure and a delay or prevention of the onset of symptoms in a subject at risk for developing glaucoma.

Interfering RNA of embodiments of the invention act in a catalytic manner, i.e., interfering RNA is able to effect inhibition of target mRNA in substoichiometric amounts. As compared to antisense therapies, significantly less interfering RNA is required to provide a therapeutic effect.

Double-stranded interfering RNA: Double stranded interfering RNA (also referred to as ds siRNA), as used herein, has a sense nucleotide sequence and an antisense nucleotide sequence, the sense and antisense sequence comprising a region of at least near-perfect contiguous complementarity of at least 19 nucleotides. The length of the interfering RNA comprises 19 to 49 nucleotides, and may comprise a length of 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides. The antisense sequence of the ds siRNA hybridizes under physiological conditions to a portion of mRNA corresponding to SEQ ID NO:1, and has a region of at least near-perfect contiguous complementarity of at least 19 nucleotides with the hybridizing portion of mRNA corresponding to SEQ ID NO:1.

The antisense strand of the siRNA is the active guiding agent of the siRNA in that the antisense strand binds to a RISC complex within a cell, and guides the bound complex to bind with specificity to the mRNA at a sequence complementary to the sequence of the antisense RNA, thereby allowing subsequent cleavage of the mRNA by the bound complex.

Techniques for selecting target sequences for siRNAs are provided by Tuschl, T. et al., "The siRNA User Guide," revised May 6, 2004, available on the Rockefeller University web site, by Technical Bulletin #506, "siRNA Design Guidelines," Ambion Inc. at Ambion's web site, by the Invitrogen web site using search parameters of min 35%, max 55% G/C content, and by the Dharmacon web site. The target sequence may be located in the coding region or a 5' or 3' untranslated region of the mRNA.

An embodiment of a DNA target sequence for CTGF is present at nucleotides 1488 to 1506 of SEQ ID NO:1:

```
nt 1488. 5'- ggttagtatcatcagatag -3'.   SEQ ID NO:18
```

A double stranded siRNA of the invention for targeting a corresponding mRNA sequence of SEQ ID NO:18 and having a 3'UU overhang on each strand is:

```
5'- gguuaguaucaucagauagUU -3'     SEQ ID NQ:25

3'- UUccaaucauaguagucuauc -5'.    SEQ ID NO:26
```

The 3' overhang may have a number of "U" residues, for example, a number of "U" residues between and including 2, 3, 4, 5, and 6. The 5' end may also have a 5' overhang of nucleotides. A double stranded siRNA of the invention for targeting a corresponding mRNA sequence of SEQ ID NO:18 and having a 3'TT overhang on each strand is:

```
5'- gguuaguaucaucagauagTT -3'     SEQ ID NQ:27

3'- TTccaaucauaguagucuauc -5'.    SEQ ID NO:28
```

The strands of a double-stranded siRNA may be connected by a hairpin loop to form a single stranded siRNA as follows:

```
5'- gguuaguaucaucagauagUUNNN\
                              N
3'- UUccaaucauaguagucuaucNNNNN/.   SEQ ID NO:29
```

N is a nucleotide A, T, C, G, U, or a modified form known by one of ordinary skill in the art. The number of nucleotides N is a number between and including 3 to 23, or 5 to 15, or 7 to 13, or 4 to 9, or 9 to 11, or the number of nucleotides N is 9.

Table 1 lists examples of CTGF DNA target sequences of SEQ ID NO:1 from which siRNAs of the present invention are designed in a manner as set forth above.

TABLE 1

CTGF Target Sequences for siRNAs

| Target Sequence | # of Starting Nucleotide with reference to SEQ ID NO:1 | SEQ ID NO: |
|---|---|---|
| GGGCCTCTTCTGTGACTTC | 379 | 2 |
| CCGACTGGAAGACACGTTT | 691 | 3 |
| CCCGGGTTACCAATGACAA | 801 | 4 |
| GGGCAAAAAGTGCATCCGT | 901 | 5 |
| TCCAAGCCTATCAAGTTTGAGCTTT | 932 | 6 |
| GCCTATCAAGTTTGAGCTT | 937 | 7 |
| GCATGAAGACATACCGAGCTAAATT | 969 | 8 |
| GCTAAATTCTGTGGAGTAT | 986 | 9 |
| GCCATTACAACTGTCCCGGAGACAA | 1119 | 10 |
| GGAAGATGTACGGAGACAT | 1170 | 11 |
| GAGAGTGAGAGACATTAACTCATTA | 1201 | 12 |
| GCCATGTCAAACAAATAGTCTATCT | 1346 | 13 |
| GGGTACCAGCAGAAAGGTT | 1473 | 14 |
| CCAGCAGAAAGGTTAGTAT | 1478 | 15 |
| GCAGAAAGGTTAGTATCAT | 1481 | 16 |
| GCAGAAAGGTTAGTATCATCAGATA | 1481 | 17 |
| GGTTAGTATCATCAGATAG | 1488 | 18 |
| GGTTAGTATCATCAGATAGCTCTTA | 1488 | 19 |
| GAGACTGAGTCAAGTTGTTCCTTAA | 1626 | 20 |
| GCAGACTCAGCTCTGACAT | 1660 | 21 |
| TCAGCTCTGACATTCTGATTCGAAT | 1666 | 22 |
| TCCTGTCGATTAGACTGGACAGCTT | 1712 | 23 |
| GCTTGTGGCAAGTGAATTT | 1733 | 24 |

As cited in the examples above, one of skill in the art is able to use the target sequence information provided in Table 1 to design interfering RNAs having a length shorter or longer than the sequences provided in Table 1 by referring to the sequence position in SEQ ID NO:1 and adding or deleting nucleotides complementary or near complementary to SEQ ID NO:1.

The target RNA cleavage reaction guided by ds or ss siRNAs is highly sequence specific. In general, siRNA containing a sense nucleotide sequence identical to a portion of the target mRNA and an antisense portion exactly complementary to the sense sequence are siRNA embodiments for inhibition of CTGF mRNA. However, 100% sequence complementarity between the antisense strand of siRNA and the target mRNA is not required to practice the present invention. Thus the invention allows for sequence variations that might be expected due to genetic mutation, strain polymorphism, or evolutionary divergence. For example, siRNA sequences with insertions, deletions, or single point mutations relative to the target sequence are effective for inhibition.

The antisense sequence of the siRNA has at least near-perfect contiguous complementarity of at least 19 nucleotides with the target sequence of the mRNA. "Near-perfect," as used herein, means the antisense sequence of the siRNA is "substantially complementary to," and the sense sequence of the siRNA is "substantially identical" to at least a portion of the target mRNA. "Identity," as known by one of ordinary skill in the art, is the degree of sequence relatedness between nucleotide sequences as determined by matching the order of nucleotides between the sequences. In one embodiment, antisense RNA having 80% and between 80% up to 100% complementarity to the target mRNA sequence are considered near-perfect complementarity and may be used in the present invention. "Perfect" contiguous complementarity is standard Watson-Crick base pairing of adjacent base pairs. "At least near-perfect" contiguous complementarity includes "perfect" complementarity as used herein. Computer methods for determining identity or complementarity are designed to provide the greatest degree of matching of nucleotide sequences, for example, BLASTP and BLASTN (Altschul, S. F., et al. (1990) *J. Mol. Biol.* 215:403-410), and FASTA.

The target sequence of SEQ ID NO:1 may be in the 5' or 3' untranslated regions of the mRNA as well as in the coding region of the mRNA.

One or both of the strands of double-stranded interfering RNA may have a 3' overhang of from 1 to 6 nucleotides which may be ribonucleotides or deoxyribonucleotides or a mixture thereof. The nucleotides of the overhang are not base-paired. In one embodiment of the invention, the interfering ds RNA comprises a 3' overhang of TT or UU.

The sense and antisense strands of the double stranded siRNA may be in a duplex formation of two single strands as described above or may be a single molecule where the regions of complementarity are base-paired and are covalently linked by a hairpin or loop so as to form a single strand. It is believed that the hairpin is cleaved intracellularly by a protein termed Dicer to form an interfering RNA of two individual base-paired RNA molecules.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, or to further improve stability. For example, interfering RNAs may comprise a purine nucleotide at the ends of overhangs. Conjugation of cholesterol to the 3' end of the sense strand of a ds siRNA molecule by means of a pyrrolidine linker, for example, also provides stability to an siRNA. Further modifications include a 3' terminal biotin molecule, a peptide known to have cell-penetrating properties, a nanoparticle, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing U with 2'deoxy-T, or having a sugar modification such as a 2'OH replaced by a 2' amino or 2" methyl group, 2'methoxyethyl groups, or a 2'-0, 4'-C methylene bridge, for example. Examples of a purine or pyrimidine analog of nucleotides include a xanthine, a hypoxanthine, an azapurine, a methylthioadenine, 7-deaza-adenosine and O— and N-modified nucleotides. The phosphate group of the nucleotide may be modified by substituting one or more of the oxygens of the phosphate group with nitrogen or with sulfur (phosphorothioates).

There may be a region of the antisense siRNA that is not complementary to a portion of mRNA corresponding to SEQ ID NO:1. Non-complementary regions may be at the 3', 5' or both ends of a complementary region.

Interfering RNAs may be synthetically generated, generated by in vitro transcription, siRNA expression vectors, or PCR expression cassettes, for example. Interfering RNAs that function well as transfected siRNAs also function well as siRNAs expressed in vivo.

Interfering RNAs are chemically synthesized using protected ribonucleoside phosphoramidites and a conventional DNA/RNA synthesizer and may be obtained from commercial suppliers such as Ambion Inc. (Austin, Tex.), Invitrogen (Carlsbad, Calif.), or Dharmacon (Lafayette, Colo., USA), for example. Interfering RNAs are purified by extraction with a solvent or resin, precipitation, electrophoresis, chromatography, or a combination thereof, for example. Alternatively, interfering RNA may be used with little if any purification to avoid losses due to sample processing.

Interfering RNA may be provided to a subject by expression from a recombinant plasmid using a constitutive or inducible promoter such as the U6 or H1 RNA pol III promoter, the cytomegalovirus promoter, SP6, T3, or T7 promoter, known to those of ordinary skill in the art. For example, the psiRNA™ from InvivoGen (San Diego, Calif.) allows production of siRNAs within cells from an RNA pol III promoter. Interfering RNA expressed from recombinant plasmids may be isolated by standard techniques.

A viral vector for expression of interfering RNA may be derived from adenovirus, adeno-associated virus, vaccinia virus, retroviruses (lentiviruses, Rhabdoviruses, murine leukemia virus, for example), herpes virus, or the like, using promoters as cited above, for example, for plasmids. Selection of viral vectors, methods for expressing the interfering RNA by the vector and methods of delivering the viral vector are within the ordinary skill of one in the art.

Expression of interfering RNAs is also provided by use of SILENCER EXPRESS™ (Ambion, Austin, Tex.) via expression cassettes (SECs) with a human H1, human U6 or mouse U6 promoter by PCR. Silencer expression cassettes are PCR products that include promoter and terminator sequences flanking a hairpin siRNA template. Upon transfection into cells, the hairpin siRNA is expressed from the PCR product and induces specific silencing.

Hybridization under Physiological Conditions. "Hybridization" refers to a technique where single-stranded nucleic acids (DNA or RNA) are allowed to interact so that hydrogen-bonded complexes called hybrids are formed by those nucleic acids with complementary or near-complementary base sequences. Hybridization reactions are sensitive and selective so that a particular sequence of interest is identified in samples in which it is present at low concentrations. The specificity of hybridization (i.e., stringency) is controlled by the concentrations of salt or formamide in the prehybridization and hybridization solutions in vitro, for example, and by the hybridization temperature, and are well known in the art. In particular, stringency is increased by reducing the concentration of salt, increasing the concentration of formamide, or raising the hybridization temperature.

For example, high stringency conditions could occur at about 50% formamide at 37° C. to 42° C. Reduced stringency conditions could occur at about 35% to 25% formamide at about 30° C. to 35° C. Examples of stringency conditions for hybridization are provided in Sambrook, J., 1989, *Molecular Cloning: A Laboratory Manual*, Cold Spring Harbor Laboratory Press, Cold Spring Harbor, N.Y. Further examples of stringent hybridization conditions include 400 mM NaCl, 40 mM PIPES pH 6.4, 1 mM EDTA, 50° C. or 70° C. for 12-16 hours followed by washing, or hybridization at 70° C. in 1×SSC or 50° C. in 1×SSC, 50% formamide followed by washing at 70° C. in 0.3×SSC, or hybridization at 70° C. in 4×SSC or 50° C. in 4×SSC, 50% formamide followed by washing at 67° C. in 1×SSC. The temperature for hybridization is about 5-10° C. less than the melting temperature ($T_m$) of the hybrid where $T_m$ is determined for hybrids between 19 and 49 base pairs in length using the following calculation: $T_m° C.=81.5+16.6(\log_{10}[Na+])+0.41$ (% G+C)$-(600/N)$ where N is the number of bases in the hybrid, and [Na+] is the concentration of sodium ions in the hybridization buffer.

In embodiments of the present invention, an antisense strand of an interfering RNA that hybridizes with CTGF mRNA in vitro under high stringency conditions will bind specifically in vivo under physiological conditions. Identification or isolation of a related nucleic acid that does not hybridize to a nucleic acid under highly stringent conditions is carried out under reduced stringency.

Single stranded interfering RNA. As cited above, interfering RNAs ultimately function as single strands. SS siRNA has been found to effect mRNA silencing, albeit less efficiently than double-stranded RNA. Therefore, embodiments of the present invention also provide for administration of ss siRNA where the single stranded siRNA hybridizes under physiological conditions to a portion of mRNA corresponding to SEQ ID NO:1, and has a region of at least near-perfect contiguous complementarity of at least 19 nucleotides with the hybridizing portion of mRNA corresponding to SEQ ID NO:1. The ss siRNA has a length of 19 to 49 nucleotides as for the ds siRNA cited above. The ss siRNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the 5' sugar (e.g., the 5' ribose or deoxyribose, or an analog of same). The ss siRNA may have a mono-, di-, or triphosphate group.

SS siRNAs are synthesized chemically or via vectors as for ds siRNAs. 5' Phosphate groups may be added via a kinase, or a 5' phosphate may be the result of nuclease cleavage of an RNA. Delivery is as for ds siRNAs. In one embodiment, ss siRNAs having protected ends and nuclease resistant modifications are administered for silencing. SS siRNAs may be dried for storage or dissolved in an aqueous solution. The solution may contain buffers or salts to inhibit annealing or for stabilization.

Hairpin interfering RNA: A hairpin interfering RNA is single-stranded and contains both the sense and antisense sequence within the one strand. For expression by a DNA vector, the corresponding DNA oligonucleotides of at least 19-nucleotides corresponding to the sense siRNA sequence are linked to its reverse complementary antisense sequence by a short spacer. If needed for the chosen expression vector, 3' terminal T's and nucleotides forming restriction sites may be added. The resulting RNA transcript folds back onto itself to form a stem-loop structure.

Mode of administration: Interfering RNA may be delivered directly to the eye by ocular tissue injection such as periocular, conjunctival, sub-Tenons, intracameral, intravitreal, subretinal, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; by a slow release device in the cul-de-sac or implanted adjacent to the sclera (transsclerahl) or within the eye. Intracameral injection may be through the cornea into the anterior chamber to allow the agent to reach the trabecular meshwork. Intracanalicular injection may be into the venous collector channels draining Schlemm's canal or into Schlemm's canal.

Subject: A subject in need of treatment for an ocular disorder or at risk for developing an ocular disorder is a human or other mammal having a condition or at risk of having a condition associated with expression or activity of CTGF, i.e., a CTGF-associated ocular disorder. Such an ocular disorder may include, for example, glaucoma, macular degeneration, diabetic retinopathy, choroidal neovascularization, proliferative vitreoretinopathy, wound healing, and conditions with excessive scarring, with endothelial cell proliferation, or fibroproliferation. Ocular structures associated with such disorders may include the retina, choroid, lens, cornea, trabecular meshwork, rod, cone, ganglia, macula, iris, sclera, aqueous chamber, vitreous chamber, ciliary body, optic disc, papilla, or fovea, for example.

Formulations and Dosage. Pharmaceutical formulations comprise an interfering RNA, or salt thereof, of the invention up to 99% by weight mixed with a physiologically acceptable ophthalmic carrier medium such as water, buffer, saline, glycine, hyaluronic acid, mannitol, and the like.

Interfering RNAs of the present invention are administered as solutions, suspensions, or emulsions. The following are examples of possible formulations embodied by this invention.

| | Amount in weight % |
|---|---|
| Interfering RNA | up to 99; 0.1-99; 0.1-50; 0.5-10.0 |
| Hydroxypropylmethylcellulose | 0.5 |
| Sodium chloride | .8 |
| Benzalkonium Chloride | 0.01 |
| EDTA | 0.01 |
| NaOH/HCl | qs pH 7.4 |
| Purified water | qs 100 mL |
| Interfering RNA | up to 99; 0.1-99; 0.1-50; 0.5-10.0 |
| Phosphate Buffered Saline | 1.0 |
| Benzalkonium Chloride | 0.01 |
| Polysorbate 80 | 0.5 |
| Purified water | q.s. to 100% |
| Interfering RNA | up to 99; 0.1-99; 0.1-50; 0.5-10.0 |
| Monobasic sodium phosphate | 0.05 |
| Dibasic sodium phosphate (anhydrous) | 0.15 |
| Sodium chloride | 0.75 |
| Disodium EDTA | 0.05 |
| Cremophor EL | 0.1 |
| Benzalkonium chloride | 0.01 |
| HCl and/or NaOH | pH 7.3-7.4 |
| Purified water | q.s. to 100% |
| Interfering RNA | up to 99; 0.1-99; 0.1-50; 0.5-10.0 |
| Phosphate Buffered Saline | 1.0 |
| Hydroxypropyl-β-cyclodextrin | 4.0 |
| Purified water | q.s. to 100% |

Generally, an effective amount of the interfering RNA of embodiments of the invention comprises an intercellular concentration at or near the ocular site of from 200 pM to 100 nM, or from 1 nM to 50 nM, or from 5 nM to about 25 nM. Topical compositions are delivered to the surface of the eye one to four times per day according to the routine discretion of a skilled clinician. The pH of the formulation is about pH 4-9, or pH 4.5 to pH 7.4.

While the precise regimen is left to the discretion of the clinician, interfering RNA may be administered by placing one drop in each eye one to four times a day, or as directed by the clinician. An effective amount of a formulation may depend on factors such as the age, race, and sex of the subject, or the severity of the ocular disorder, for example. In one embodiment, the interfering RNA is delivered topically to the eye and reaches the trabecular meshwork, retina or optic nerve head at a therapeutic dose thereby ameliorating a CTGF-associated disease process.

Acceptable carriers. An ophthalmically acceptable carrier refers to those carriers that cause at most, little to no ocular irritation, provide suitable preservation if needed, and deliver one or more interfering RNAs of the present invention in a homogenous dosage. An acceptable carrier for administration of interfering RNA of embodiments of the present invention include the Mirus TransIT®-TKO siRNA Tranfection Reagent (Mirus Corporation, Madison, Wis.), LIPOFECTIN®, lipofectamine, OLIGOFECTAMINE™ (Invitrogen, Carlsbad, Calif.), CELLFECTIN®, DHARMAFEC™ (Dharmacon, Chicago, Ill.) or polycations such as polylysine, liposomes, or fat-soluble agents such as cholesterol. Liposomes are formed from standard vesicle-forming lipids and a sterol, such as cholesterol, and may include a targeting molecule such as a monoclonal antibody having binding affinity for endothelial cell surface antigens, for example. Further, the liposomes may be PEGylated liposomes.

For ophthalmic delivery, an interfering RNA may be combined with ophthalmologically acceptable preservatives, cosolvents, surfactants, viscosity enhancers, penetration enhancers, buffers, sodium chloride, or water to form an aqueous, sterile ophthalmic suspension or solution. Ophthalmic solution formulations may be prepared by dissolving the inhibitor in a physiologically acceptable isotonic aqueous buffer. Further, the ophthalmic solution may include an ophthalmologically acceptable surfactant to assist in dissolving the inhibitor. Viscosity building agents, such as hydroxymethyl cellulose, hydroxyethyl cellulose, methylcellulose, polyvinylpyrrolidone, or the like, may be added to the compositions of the present invention to improve the retention of the compound.

In order to prepare a sterile ophthalmic ointment formulation, the interfering RNA is combined with a preservative in an appropriate vehicle, such as mineral oil, liquid lanolin, or white petrolatum. Sterile ophthalmic gel formulations may be prepared by suspending the interfering RNA in a hydrophilic base prepared from the combination of, for example, CARBOPOL®-940 (BF Goodrich, Charlotte, N.C.), or the like, according to methods known in the art for other ophthalmic formulations. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.), in the event the interfering RNA is less penetrating in the eye.

Kits: Embodiments of the present invention provide a kit that includes reagents for attenuating the expression of a CTGF mRNA in a cell. The kit contains a DNA template that has two different promoters such as a T7 promoter, a T3 promoter or an SP6 promoter, each operably linked to a nucleotide sequence that encodes two complementary single-stranded RNAs corresponding to an interfering RNA. RNA is transcribed from the DNA template and is annealed to form a double-stranded RNA effective to attenuate expression of the target mRNA. The kit optionally contains amplification primers for amplifying the DNA sequence from the DNA template and nucleotide triphosphates (i.e., ATP, GTP, CTP and UTP) for synthesizing RNA. Optionally, the kit contains two RNA polymerases, each capable of binding to a promoter on the DNA template and effecting transcription of the nucleotide sequence to which the promoter is operably linked, a purification column for purifying single-stranded RNA, such as a size exclusion column, one or more buffers, for example, a buffer for annealing single-stranded RNAs to yield double stranded RNA, and RNAse A or RNAse T for purifying double stranded RNA.

EXAMPLE 1

Interfering RNA for Silencing CTGF in Trabecular Meshwork Cells and Criteria for Measuring Silencing The present study examines the ability of CTGF interfering RNA to knock-down the levels of endogenous CTGF expression in human trabecular meshwork (TM) cells. The present study also provides criteria for determining the efficacy of interfering RNA on mRNA levels when QPCR primers are used for measurement.

Transfection of a transformed human TM cell line designated GTM3 or HTM-3 (see Pang, I. H. et al.,. 1994. *Curr. Eye Res.* 13:51-63) was accomplished using standard in vitro concentrations of CTGF interfering RNA (100 nM) and LIPOFECTAMINE™ 2000 (Invitrogen, Carlsbad, Calif.) at a 1:1 (w/v) ratio. A pool of commercially designed interfering RNAs of unknown sequence (siGENOME SMARTPOOL® CTGF interfering RNA (designated siRNA S4 herein), Dharmacon, Lafayette, Colo.) was used to target CTGF. Scrambled and lamin A/C siRNA (Dharmacon) were used as controls.

Control experiments resulted in close to 90% knock-down efficiency of lamin A/C using lamin A/C interfering RNA when compared to the scrambled interfering RNA control. Initial studies showed an efficiency of knock-down of CTGF of about 20-30% when using siGENOME SMARTPOOL® CTGF siRNA M-012633-00-0020 (siRNA S4) using primer/probe set Q2 directed to the CTGF mRNA 3'UTR in exon 5 (FIG. 2B). Q2 is a QPCR TAQMAN® & primer/probe sets from ABI (Applied Biosystems, Foster City, Calif.).

To determine the reason for the poor CTGF siRNA efficacy, several variables were tested. Dose response with the CTGF interfering RNA was tested to determine if a suboptimal interfering RNA concentration or a suboptimal interfering RNA:lipid ratio was being used. Resultant data indicated poor CTGF mRNA knock-down regardless of the interfering RNA concentration or interfering RNA: lipid ratio employed. Given the importance of cellular uptake on siRNA activity and the inherent difficulty of transfecting TM cells, the TM cell transfection efficiency was determined under the above-cited conditions. Transfection efficiency was examined as a reflection of either cell death induced by SITOX™ (Dharmacon) delivery to the cell cytoplasm or cell fluorescence as measured by cytoplasmic fluorescence with SIGLO™ (Dharmacon). In both cases, nearly all cells were either dead (FIG. 1A; SITOX™) or fluorescent (FIG. 1B; SIGLO™), suggesting that the transfection efficiency was nearly quantitative and not the rate-limiting step in the process.

Further, three additional individual CTGF siRNA sequences from Ambion Inc. (Austin, Tex.) designated siRNA S1, S2, and S3 were tested in combination with two different QPCR TAQMAN® primer/probe sets designated Q2 and Q1 (ABI, Applied Biosystems, Foster City, Calif.). The target sequences for Ambion siRNAs are as follows using GenBank reference sequence number NM_001901 for nucleotides (nts) of CTGF:

```
target for S1: (nts 379-397):
gggcctcttctgtgacttc         SEQ ID NO:2 target for S2: (nts 901-919):
gggcaaaaagtgcatccgt         SEQ ID NO:5 target for S3: (nts 1488-1506):
ggttagtatcatcagatag         SEQ ID NO:18
```

Double stranded siRNA with a 3'TT overhang on each strand for each of the above targeted sequences are:

```
siRNA Si:
5'-gggccucuucugugacuucTT-3'    SEQ ID NO:30

3'-TTcccggagaagacacugaag-5'    SEQ ID NO:31 siRNA S2:
5'-gggcaaaaagugcauccguTT-3'    SEQ ID NO:32

3'-TTcccguuuuucacguaggca-5'    SEQ ID NO:33 siRNA S3:
5'-gguuaguaucaucagauagTT-3'    SEQ ID NO:27

3'-TTccaaucauaguagucuauc-5'    SEQ ID NO:28
```

The QPCR Q1 primer is a proprietary sequence from ABI ASSAY ON DEMAND™ Hs00170014_ml (Applied Biosystems).

The QPCR Q2 forward primer has the sequence:

```
5'-CAGCTCTGACATTCTGATTCGAA-3'    SEQ ID NO:34
``` and the Q2 reverse primer has the sequence:

```
5'-TGCCACAAGCTGTCCAGTCT-3'    SEQ ID NO:35
```

The Q2 probe has the sequence:
5'-AATCGACAGGATTCCGATTCCTGAACAGTG-3'
SEQ ID NO:36 and has an FAM group at the 5' end (6-carboxyfluorescein) and a TAMRA group at the 3' end (Applied Biosystems).

The location of the primer/probe sets in relation to the siRNA target sites for the individual siRNAs is shown in FIG. 2A. Also shown in the schematic of FIG. 2A are the CTGF gene exon (boxes) and intron (lines) structure and location of siRNAs S1, S2, and S3 and QPCR primer/probe sets Q1 and Q2 in relation to the GenBank CTGF sequence NM_001901, the sequence of which is provided as SEQ ID NO:1.

FIG. 2B shows QPCR amplification of CTGF mRNA using the exon 5 primer/probe set Q2 and siRNAs S1-S4. Using the S1 and S4 siRNAs, no significant knock-down of the CTGF mRNA levels was detected with the Q2 primer/probe set. Knock-down was demonstrated by siRNAs S2 and S3. The primer/probe set Q2 has closer proximity to the targets of the S2 and S3 siRNAs as compared to the target of the S1 siRNA.

FIG. 2C shows QPCR amplification of CTGF mRNA using the exon 4/5 spanning primer/probe set Q1. Knock-down of CTGF mRNA was demonstrated by each of the siRNAs and an ~90% knock-down was observed with the S2 siRNA using the Q1 primer/probe set for detection. The primer/probe set Q1 appears to be more efficient at demonstrating knock-down by the siRNAs as compared to the Q2 primer probe set.

The data of FIGS. 2B and 2C suggest that the particular region amplified using the 3'-UTR-directed primer/probe set Q2 may be relatively stable and thus a poor choice for assessing the cleavage and degradation of the CTGF mRNA by the targeting siRNA. Therefore, siRNA efficacy may be underreported in specific cases where the QPCR amplification region lies outside the siRNA targeting region.

To reduce the chance of non-specific, off-target effects, the lowest possible siRNA concentration for inhibiting CTGF mRNA expression was determined. CTGF mRNA knockdown was assessed by QPCR amplification using primer/probe set Q1. A dose response of CTGF S2 siRNA in GTM3 cells is shown in FIG. 3. An $IC_{50}$ of ~2.5 nM was observed in GTM3 cells after 24 hour treatment with 0, 1, 3, 10, 30, and 100 nM dose range of S2 siRNA. Data were fitted using GraphPad Prism 4 software (GraphPad Software, Inc., San Diego, Calif.) with a variable slope, sigmoidal dose response algorithm and a top constraint of 100%.

The results of this example demonstrate that i) trabecular meshwork cells carry out siRNA silencing, ii) all of the siRNAs cited herein effect a degree of silencing, and iii) when using a PCR-based approach to determine the efficacy of siRNA knock-down, the PCR amplification primers are designed to encompass the siRNA targeting sequence for optimum detection of silencing.

Cleavage of target mRNA by the RISC endonuclease has been shown to occur near the center of the siRNA targeting sequence (Elbashir, S. M., et al., 2001. *Genes Dev* 15:188-200) and is accomplished by Argonaute RNaseH activity (Liu, J., et al., 2004. *Science* 305:1437-1441). However, complete degradation of the remaining mRNA appears not to be guaranteed. Stable fragments of mRNA may remain following Argonaute cleavage and amplification of one of these fragments by QPCR may underreport the siRNA efficacy as shown herein. The present invention provides an embodiment where QPCR primer sets encompass the siRNA target sequence to ensure optimum siRNA efficiency readout.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

As used herein and unless otherwise indicated, the terms "a" and "an" are taken to mean "one", "at least one" or "one or more".

What is claimed is:

1. A method of attenuating expression of connective tissue growth factor mRNA in an eye of a subject, said method comprising:
   administering by ocular injection to said eye of said subject a composition comprising an effective amount of an interfering RNA consisting of a length of 21 to 49 nucleotides and a pharmaceutically acceptable carrier, said interfering RNA comprising:
   5'-gggcaaaaagugcauccguTT-3' SEQ ID NO: 32 (sense nucleotide sequence) and 3'-TTcccguuuuucacguaggca-5' SEQ ID NO: 33 (antisense nucleotide sequence), wherein the expression of connective tissue growth factor mRNA is attenuated.

2. The method of claim 1, wherein said subject has a connective tissue growth factor-associated ocular disorder or is at risk of developing a connective tissue growth factor-associated ocular disorder.

3. The method of claim 2, wherein said connective tissue growth factor-associated ocular disorder is glaucoma.

4. The method of claim 1, wherein said sense nucleotide sequence and said antisense nucleotide sequence are connected by a loop nucleotide sequence.

5. The method of claim 1, wherein said composition is administered via a topical, intravitreal, or transcleral route.

6. The method of claim 1, further comprising administering by ocular injection to said eye of said subject a second interfering RNA consisting of a length of 19 to 49 nucleotides, and comprising a sense nucleotide sequence, an antisense nucleotide sequence, and a region of at least near-perfect complementarity of at least 19 nucleotides; wherein said antisense nucleotide sequence of said second interfering RNA has a region of at least near-perfect contiguous complementarity of at least 19 nucleotides with a second portion of mRNA corresponding to SEQ ID NO: 1.

7. A method of treating glaucoma in a subject in need thereof, said method comprising:
   administering by ocular injection to an eye of said subject a composition comprising an effective amount of an interfering RNA consisting of a length of 21 to 49 nucleotides and a pharmaceutically acceptable carrier, said interfering RNA comprising:
   5'-gggcaaaaagugcauccguTT-3' SEQ ID NO: 32 (sense nucleotide sequence) and 3'-TTcccguuuuucacguaggca-5' SEQ ID NO: 33 (antisense nucleotide sequence), wherein said glaucoma is treated thereby.

8. The method of claim 7, wherein said sense nucleotide sequence and said antisense nucleotide sequence are connected by a loop nucleotide sequence.

9. The method of claim 7, wherein said composition is administered via a topical, intravitreal, or transcleral route.

10. The method of claim 7, further comprising administering by ocular injection to said eye of said subject a second interfering RNA consisting of a length of 19 to 49 nucleotides, and comprising a sense nucleotide sequence, an antisense nucleotide sequence, and a region of at least near-perfect complementarity of at least 19 nucleotides; wherein said antisense nucleotide sequence of said second interfering RNA has a region of at least near-perfect contiguous complementarity of at least 19 nucleotides with a second portion of mRNA corresponding to SEQ ID NO: 1.

* * * * *